United States Patent
Ohashi (10) Patent No.: US 8,149,376 B2
(45) Date of Patent: Apr. 3, 2012

(54) TEST DATA PROCESSING APPARATUS AND TEST DATA PROCESSING METHOD

(75) Inventor: Hiromichi Ohashi, Ibaraki (JP)

(73) Assignee: Nitto Denko Corporation, Ibaraki-shi, Osaka (JP)

( * ) Notice: Subject to any disclaimer, the term of this patent is extended or adjusted under 35 U.S.C. 154(b) by 914 days.

(21) Appl. No.: 11/870,110

(22) Filed: Oct. 10, 2007

(65) Prior Publication Data

US 2008/0088790 A1    Apr. 17, 2008

(30) Foreign Application Priority Data

Oct. 11, 2006  (JP) ................................. 2006-277922
Jul. 12, 2007  (JP) ................................. 2007-183470

(51) Int. Cl.
*G02F 1/13*    (2006.01)
(52) U.S. Cl. ..................................................... 349/192
(58) Field of Classification Search .................. None
See application file for complete search history.

(56) References Cited

U.S. PATENT DOCUMENTS

| | | | |
|---|---|---|---|
| 2005/0096431 A1 | 5/2005 | Fujii et al. | |
| 2005/0167620 A1 | 8/2005 | Cho et al. | |

FOREIGN PATENT DOCUMENTS

| | | |
|---|---|---|
| JP | 11-311510 A | 11/1999 |
| JP | 11-326224 A | 11/1999 |
| JP | 2001-343529 A | 12/2001 |
| JP | 2004-170495 A | 6/2004 |
| JP | 2005-49158 A | 2/2005 |
| JP | 2005-62165 A | 3/2005 |
| JP | 2005-181070 A | 7/2005 |
| JP | 2008-020588 A | 1/2008 |
| WO | 2006/029536 A1 | 3/2006 |

OTHER PUBLICATIONS

European Search Report dated Dec. 23, 2009, issued in corresponding European Patent Application No. 07117705.9.
Japanese Office Action dated Aug. 23, 2011, issued in corresponding Japanese Patent Application No. 2007-183470.

*Primary Examiner* — Timothy L Rude (57) ABSTRACT

The test data processing apparatus of the present invention is a test data processing apparatus for processing test data obtained by testing defects of a sheet-shaped product having at least an optical film which is a member of an optical displaying apparatus, comprising a defect information preparing section, wherein, on the basis of surface defect test data relating to a surface defect and bright point test data relating to a bright point obtained when the optical film or a laminate body containing the optical film is regarded as an object of testing, in a case that a position of the surface defect and a position of the bright point are identical, the surface defect and the bright point located at the identical position are not regarded as a defect for processing by the defect information preparing section.

11 Claims, 4 Drawing Sheets

[FIG.2]

<INFORMATION OF DEFECTS BY REFLECTED LIGHT IMAGE>

| COORDINATES | KIND OF DEFECT | SIZE (μm) | SHAPE |
|---|---|---|---|
| x1,y1 | SURFACE-ADHERING FOREIGN SUBSTANCE | 3 | TRIANGLE |
| x3,y3 | SURFACE-ADHERING FOREIGN SUBSTANCE | 10 | CIRCLE |
| x4,y4 | SURFACE-ADHERING FOREIGN SUBSTANCE | 3 | FOREIGN SHAPE |
| ... | ... | ... | ... |

<INFORMATION OF DEFECTS BY 0 DEGREES CROSS>

| COORDINATES | KIND OF DEFECT | SIZE (μm) | SHAPE |
|---|---|---|---|
| x1,y1 | BRIGHT POINTS | 2 | CIRCLE |
| x3,y3 | BRIGHT POINTS | 10 | QUADRILATERAL |
| x4,y4 | BRIGHT POINTS | 3 | FOREIGN SHAPE |
| x5,y4 | BRIGHT POINTS | 4 | QUADRILATERAL |
| ... | ... | ... | ... |

| SAME COORDINATES | SAME SIZE | SAME SHAPE |
|---|---|---|
| (x1,y1) | NO | NO |
| (x3,y3) | YES | NO |
| (x4,y4) | YES | YES |

<INFORMATION OF DEFECTS BY TRANSMITTED LIGHT IMAGE>

| COORDINATES | KIND OF DEFECT | SIZE (μm) | SHAPE |
|---|---|---|---|
| x10,y10 | INTERNAL FOREIGN SUBSTANCE | ... | ... |
| x11,y12 | INTERNAL FOREIGN SUBSTANCE | ... | ... |
| x13,y13 | INTERNAL FOREIGN SUBSTANCE | ... | ... |
| x14,y14 | INTERNAL FOREIGN SUBSTANCE | ... | ... |
| ... | ... | ... | ... |

<INFORMATION OF DEFECTS BY x DEGREES CROSS>

| COORDINATES | KIND OF DEFECT | SIZE (μm) | SHAPE |
|---|---|---|---|
| x21,y21 | KNICKS | 2 | ... |
| x22,y22 | KNICKS | 4 | ... |
| x23,y23 | KNICKS | 10 | ... |
| x24,y24 | KNICKS | 3 | ... |
| ... | ... | ... | ... |

<PREPARED DEFECT INFORMATION>

| COORDINATES | KIND OF DEFECT | SIZE (μm) | SHAPE |
|---|---|---|---|
| x5,y4 | BRIGHT POINTS | 4 | QUADRILATERAL |
| x10,y10 | INTERNAL FOREIGN SUBSTANCE | ... | ... |
| x11,y12 | INTERNAL FOREIGN SUBSTANCE | ... | ... |
| x13,y13 | INTERNAL FOREIGN SUBSTANCE | ... | ... |
| x14,y14 | INTERNAL FOREIGN SUBSTANCE | ... | ... |
| x21,y21 | KNICKS | 2 | ... |
| x22,y22 | KNICKS | 4 | ... |
| x23,y23 | KNICKS | 10 | ... |
| x24,y24 | KNICKS | 3 | ... |
| ... | ... | ... | ... |

[FIG.4] PRIOR ART

POLARIZER PROTECTIVE FILM
POLARIZER
POLARIZER PROTECTIVE FILM
PROTECTIVE FILM
SEPARATOR

TEST DATA PROCESSING APPARATUS AND TEST DATA PROCESSING METHOD

BACKGROUND OF THE INVENTION

1. Field of the Invention

The present invention relates to a test data processing apparatus and a test data processing method for processing test data obtained by testing defects of a sheet-shaped product having at least an optical film that is a member of an optical displaying apparatus.

2. Description of the Background Art

Conventionally, in a maker for producing an optical film, a band-shaped sheet-shaped product having an optical film member is produced by collecting and winding it in a roll form or on a different production line for each step. As this "band-shaped sheet-shaped product", there are, for example, a polarizing plate source, a retardation plate source, and a laminate film source of a polarizing plate and a retardation plate used in a liquid crystal display device.

An adhesive agent is used for bonding this sheet-shaped product with an optical displaying unit. This adhesive agent is formed in advance as an adhesive layer on the sheet-shaped product, and further a release film (which may also be referred to as a separator) is formed for protection of the adhesive layer.

Figure 4:
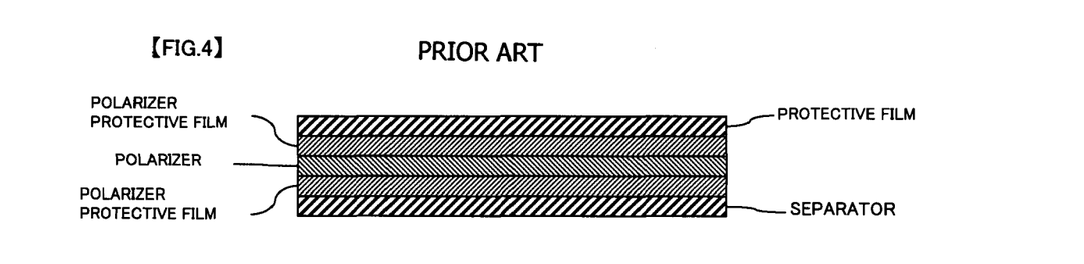
FIG. 4 is a view describing a construction of a sheet-shaped product having a polarizing plate.

A conventional example of the steps for producing a sheet-shaped product having a polarizing plate with a laminate structure of FIG. 4 will be described below. First, as preliminary steps, there are (A) a step of obtaining a polarizer, where the polarizer is obtained by drying a polyvinyl alcohol (PVA) film subjected to a dyeing/crosslinking and stretching process, (B) a step of producing a polarizing plate, where the polarizing plate is produced by bonding a triacetylcellulose (TAC) film via an adhesive agent on both surfaces of the polarizer and laminating a polarizer protective layer; here, in the drawings, an antiglare process is performed in advance on the TAC film to be laminated thereon, (C) a step of bonding a separator and a protective film, where the separator is bonded via a strong adhesive agent on one surface of the polarizing plate (lower side in the drawings) and the protective film is bonded via a weak adhesive agent on the other surface (upper side in the drawings). Here, the strong adhesive agent is applied in advance on the separator, and the weak adhesive agent is applied in advance on the protective film. The strong adhesive agent applied on the separator is transferred to the TAC after releasing the separator. The weak adhesive agent applied on the protective film remains as it is formed on the protective film after releasing the protective film, so that substantially the weak adhesive agent is not transferred to the TAC. Through the above-described preliminary steps, a band-shaped sheet-shaped product is produced, collected and wound in a roll form, and subjected to subsequent processes.

In these preliminary steps (A, B, C), a predetermined test is carried out for each step by a testing person. For example, in the case of the step (A), during the transportation of the PVA source, the testing person confirms the defects (foreign substances, stains, twists, and the like) by eye inspection. Also, in the case of the step (B), in collecting and winding the obtained polarizing plate source in a roll form, the testing person confirms the defects (foreign substances, stains, knicks, twists, creases, and the like) by eye inspection at the timings of the start and the end of winding of the roll. Also, the polarizing plate source after bonding is automatically tested by a defect testing apparatus (a known apparatus for capturing images of foreign substances, stain, and the like with a camera, and determining the defects by image processing); the defects are confirmed by a monitor; and the test was mainly used for state management (supervision) by monitoring the defects.

Also, in the case of the step (C), in collecting and winding the obtained band-shaped sheet-shaped product source in a roll form, the testing person confirms the defects (foreign substances, stain, twist, surface-adhering substances, and the like) by eye inspection at the timings of the start and the end of winding of the roll, and performed the ranking (good, bad, permissibility of shipping) of the sheet-shaped product source by evaluating these defects.

Subsequently, as the posterior steps, there is (D) a step of testing the source roll. Here, the appearance of the sheet-shaped product roll is tested by a roll-form automatic source testing apparatus and/or by eye inspection of a testing person. The roll-form automatic source testing apparatus is a known apparatus that captures images of poor winding, poor appearance, and the like with a camera, and performs image processing to determine the defects. Also, there is (E) a step of cutting into a sheet-shaped product provided in separate sheets. Here, a sheet-shaped product is drawn out from the source roll, and is cut to have a predetermined size. As the cutting method, there are, for example, constant-measure cutting, continuous punching-out, and the like. Also, there is (F) a step of testing the sheet-shaped product provided in separate sheets. Herein, testing by a sheet-form automatic testing apparatus and by eye inspection of a testing person are carried out. The sheet-form automatic testing apparatus is an apparatus that automatically tests the defects of a sheet-shaped product provided in separate sheets, where light is radiated; images of the reflected light thereof or images of transmitted light thereof are captured with an imaging section such as a line sensor or a two-dimensional TV camera; and the defects are detected on the basis of the captured image data. Also, the image data are obtained in a state in which a polarizing filter for testing intervenes in the optical path between the light source and the imaging section. Typically, the polarization axis (for example, the polarization absorption axis) of this polarizing filter for testing is disposed to be in a state (crossed nicol form) perpendicular to the polarization axis (for example, the polarization absorption axis) of the polarizing plate that is an object of testing. By disposing it in crossed nicol, an image of total black is input from the imaging section if there are no defects; however, when there are defects, that part will not be black (and will be recognized as bright points). Therefore, the defects can be detected by setting a suitable threshold value.

As described above, in the posterior steps (D, E, F), the sheet-shaped product source wound in a roll form is drawn out and is cut into a sheet-shaped product provided in separate sheets of a predetermined size, followed by a predetermined defect testing to determine the quality for shipping.

As described above, in the previous steps, the testing of defects is carried out with a defect testing apparatus after forming the polarizing plate. In the steps, generally, a polarization filter for testing is disposed between the object of testing and the CCD camera, and bright points are detected by setting the polarization axis with the object of testing to be in a state of crossed nicol (0 degree cross). In detecting the bright points, the defects such as surface-adhering substances and internal foreign substances are detected as bright points. Also, in addition to this bright point detection, a method is adopted in which foreign substances are detected by capturing a transmitted light image of an object with a CCD camera and performing image analysis. Also, a method is adopted in which surface-adhering foreign substances are detected by capturing a reflected light image of an object with a CCD camera and performing image analysis.

Also, a sheet-shaped product testing system and a sheet-shaped product producing system described below are known (See Japanese Patent Application Laid-Open (JP-A) No. 2005-62165). The defects of a band-shaped polarizing plate source are detected; the position information of these defects is printed in a form of a bar code at the width-direction end part of the polarizing plate source; and the band-shaped polarizing plate source having the bar code recorded thereon is collected and wound in a roll form. Then, the band-shaped polarizing plate source is drawn out from the roll; the bar code printed at the width-direction end part of the polarizing plate source is detected; the site of the defects is marked on the basis of this bar code; and individual polarizing plates can be punched out from the polarization source after this marking. The punched and marked polarizing plates containing the defects are determined as bad products.

In the meantime, in accordance with the development of image capturing technique and image analyzing technique of recent years, the defects in μm units can be detected. Also, due to the demand for higher product quality and higher image quality of the displaying apparatus, there is a need for raising the precision of defect testing.

As described above, the steps of producing a sheet-shaped product are complex and made of numerous steps. In addition, the sheet-shaped product has a large width, has a large length, and is drawn out from the source in a roll form in each production step for performing the process of each step. Namely, the sheet-shaped product is drawn out in a band shape, and is collected and wound in a roll form again after the process is finished. During that period, the sheet surface is exposed to the outside, so that the sheet-shaped product is liable to be contaminated from the outside. In particular, there are cases in which the litters and dusts in the air may adhere to the surface, or the foreign substances in the processing liquid may adhere, followed by being dried as they are. However, these foreign substances adhering to the surface will not be the final defects by being forcibly removed in a later step (for example, removal by suction, removal by electrostatic adsorption, or the like, or by being subjected to a surface cleaning treatment or the like).

When the surface-adhering substances are determined as defects in this manner, the number of taking the sheet-shaped products will decrease, thereby raising a problem of lowering the yield. Also, in the case of producing a sheet-shaped product using the method of JP-A No. 2005-62165, the defects of the surface-adhering foreign substances are determined, as they are, as defects, are marked, and are treated as bad products after being punched out, thereby giving a cause of decrease in the yield.

In order to solve this, a method of determining whether the defects are surface-adhering foreign substances or not by image analyzing process or the like may be considered; however, this requires a complex algorithm and the data processing itself will be complex, hence not preferable.

The present invention has been made in view of the above, and an object thereof is to provide a test data processing apparatus and a test data processing method that determine the defects of surface-adhering foreign substances easily and perform data processing without treating the surface-adhering foreign substances as defects, by using a conventional testing method.

In order to solve the above-described problems of the prior art, the inventors of the present invention have made eager studies and, as a result, completed the following invention.

SUMMARY OF THE INVENTION

The test data processing apparatus of the present invention is a test data processing apparatus for processing test data obtained by testing defects of a sheet-shaped product having at least an optical film which is a member of an optical displaying apparatus, comprising a defect information preparing section, wherein, on the basis of surface defect test data relating to a surface defect and bright point test data relating to a bright point obtained when the optical film or a laminate body containing the optical film is regarded as an object of testing, in a case that a position of the surface defect and a position of the bright point are identical, the surface defect and the bright point located at the identical position are not regarded as a defect for processing by the defect information preparing section.

The functions and effects of the above-described construction are as follows. The test data processing apparatus has a function of processing test data obtained by testing defects of a sheet-shaped product having at least an optical film which is a member of an optical displaying apparatus. Then, on the basis of surface defect test data relating to a surface defect and bright point test data relating to a bright point obtained when the optical film or a laminate body containing the optical film is regarded as an object of testing, in a case that a position of the surface defect and a position of the bright point are identical, the defect information preparing section does not regard the surface defect and the bright point located at the identical position as a defect for processing.

This allows that, since the defects of surface-adhering foreign substances are not treated as defects, the data processing capability will be improved. In the conventional cases, since the surface-adhering substances are treated as defects, there has been decrease in the production yield. In contrast, according to the present invention, the surface-adhering substances are not treated as defects, thereby leading to a great improvement in the production yield and in the number of taking the products.

Also, in the present invention, it is preferable that, when the defect and the bright point located at an identical position have an identical or approximately identical size and/or shape, the surface defect and the bright point located at the identical position are not regarded as a defect for processing by the test data processing apparatus.

This allows that, by performing the determination of having an identical or approximately identical size and/or shape or not in addition to the determination of being located at an identical position, the determination of being a surface-adhering foreign substance can be carried out with a higher precision. Also, a polarizer can be raised as the optical film of the present invention.

Also, another test data processing method of the present invention is a test data processing method for processing test data obtained by testing defects of a sheet-shaped product having at least an optical film which is a member of an optical displaying apparatus, wherein, on the basis of surface defect test data relating to a surface defect and bright point test data relating to a bright point obtained when the optical film or a laminate body containing the optical film is regarded as an object of testing, in a case that a position of the surface defect and a position of the bright point are identical, the surface defect and the bright point located at the identical position are not regarded as a defect for processing.

In the above-described test data processing method, it is preferable that, when the defect and the bright point located at an identical position have an identical or approximately identical size and/or shape, the surface defect and the bright point located at the identical position are not regarded as a defect for processing.

The functions and effects of this test data processing method are similar to the functions and effects described in the above test data processing apparatus.

In the present invention, the "defects" mean, for example, stains on the surface or on the inside, scars, special defects (which may be referred to as knicks) that are in a form of twisted wounds that have bitten foreign substances, air bubbles, foreign substances, and the like.

The "test data" are information such as information relating to the kind of the defects and information relating to the coordinates of the defects. The "defect information" is, for example, information such as information relating to the kind of the defects, coordinates of the defects, production identification information, and test object identification information. The test data or the defect information can be used for producing (for example, slitting or cutting) a sheet-shaped product in a roll form or in separate sheets.

BRIEF DESCRIPTION OF THE DRAWINGS

FIG. 2 is a view describing the procedure of preparing defect information;

DETAILED DESCRIPTION OF THE PREFERRED EMBODIMENTS

Hereinafter, preferable embodiments of the present invention will be described.
<Sheet-Shaped Product>

As an example of the sheet-shaped product dealt with in the present invention, a polarizing plate source will be described. The polarizing plate source is formed in a long band shape, and polarizing plates having individual sizes can be obtained by punching out (or cutting) from the polarizing plate source in a film form. The polarizing plate source can be obtained by bonding, for example, a triacetylcellulose film (transparent polarizer protective layer) on both of the front and rear surfaces of a polyvinyl-alcohol-based film (polarizer) that has been produced in advance. It is necessary to detect the defects (scars, foreign substances, knicks, stains, and the like) that are present on the surface or in the inside of the polarizing plate source made to have a multiple layer structure. These can be detected by detecting means described later.

As described also in the prior art section, the polarizing plate source is produced by a production method including (A) a step of obtaining a polarizer, (B) a step of producing a polarizing plate, and (C) a step of bonding a separator and a protective film.

The processes of dyeing, crosslinking, and stretching the polyvinyl-alcohol-based film need not be carried out separately, but may be carried out simultaneously. Also, the order of the processes may be arbitrary. Herein, as the polyvinyl-alcohol-based film, a polyvinyl-alcohol-based film subjected to a swelling process may be used. Generally, a polyvinyl-alcohol-based film is immersed into a solution containing iodine or a dichroic dye so as to let the iodine or the dichroic dye be adsorbed for dyeing and, after being washed, subjected to monoaxial stretching in a solution containing boric acid, borax, or the like in a stretching magnification of 3 times to 7 times, followed by drying. By drying after being stretched in a solution containing iodine or a dichroic dye and after being further stretched (two-step stretching) in a solution containing boric acid, borax, or the like, the orientation of iodine will be high, and the polarization degree characteristics will be good, so that it is especially preferable.

Examples of the above-described polyvinyl-alcohol-based polymer are those obtained by polymerizing vinyl acetate and then performing saponization, those obtained by copolymerizing a small amount of polymerizable polymers such as unsaturated carboxylic acid, unsaturated sulfonic acid, and cationic monomers with vinyl acetate, and the like. The average polymerization degree of the polyvinyl-alcohol-based polymer is not particularly limited, so that those having an arbitrary polymerization degree can be used; however, the polymerization degree is preferable 1000 or higher, more preferably 2000 to 5000. Also, the saponization degree of the polyvinyl-alcohol-based polymer is preferably 85 mol % or higher, more preferably 98 to 100 mol %.

The thickness of the polarizer to be produced is typically 5 to 80 μm; however, it is not limited to this alone. Also, the method of adjusting the thickness of the polarizer is not particularly limited, so that ordinary methods such as tenter, roll stretching, and press-rolling can be used.

The process of bonding the polarizer and a transparent polarizer-protective layer constituting the protective layer is not particularly limited, so that it can be carried out, for example, via an adhesive made of a polyvinyl-alcohol-based polymer, an adhesive made of at least a water-soluble crosslinking agent of the polyvinyl-alcohol-based polymer such as boric acid, borax, glutaraldehyde, melamine, or oxalic acid. Such an adhesive layer is formed as a layer obtained by applying and drying an aqueous solution; however, in preparing the aqueous solution, other additives and catalysts such as acid can be blended in accordance with the needs.

As the polarizer protective layer disposed on one side or on both sides of the polarizer, a suitable transparent film can be used. Among these, a film made of a polymer being excellent in transparency, mechanical strength, thermal stability, water-shielding property, and the like is preferably used. Examples of the polymer are acetate-based resin such as triacetylcellulose, polycarbonate-based resin, polyester-based resin such as polyallylate or polyethylene terephthalate, polyimide-based resin, polysulfone-based resin, polyethersulfone-based resin, polystyrene-based resin, polyolefin-based resin such as polyethylene or polypropylene, polyvinylalcohol-based resin, polyvinyl-chloride-based resin, polynorbornene-based resin, polymethyl-methacrylate-based resin, liquid crystal polymer, and the like. The film may be produced by any of the casting method, the calendaring method, and the extrusion method.

Also, another example of the film is a polymer film disclosed in Japanese Patent Application Laid-Open (JP-A) No. 2001-343529 (WO01/37007), for example, a resin composition containing (A) a thermoplastic resin having a substituted and/or non-substituted imide group in a side chain and (B) a thermoplastic resin having substituted and/or non-substituted phenyl and nitrile groups in a side chain. A specific example is a film made of a resin composition containing an alternate copolymer of isobutyrene and N-methylmaleimide and an acrylonitrile/styrene copolymer. As the film, a film made of a mixed and extruded product of the resin composition can be used. Since these films have only a small retardation and a small optical elastic modulus, inconveniences such as unevenness caused by the distortion of the polarizing plate can be eliminated. Also, since the humidity transmitting degree is small, the film is excellent in the durability against addition of moisture.

Also, the polarizer protective layer is preferably colored as little as possible. Therefore, a protective film in which the retardation value in the film thickness direction represented by $Rth=[(nx+ny)/2-nz] \cdot d$ (where nx and ny are principal refractive indices within the film plane; nz is a refractive index in a film thickness direction; and d is the film thickness) is −90 nm to +75 nm is preferably used. By using such a film in which the retardation value (Rth) in the thickness direction is −90 nm to +75 nm, the coloring (optical coloring) of the polarizing plate caused by the protective film can be almost completely eliminated. The retardation value (Rth) in the thickness direction is more preferably −80 nm to +60 nm, most preferably −70 nm to +45 nm.

In view of the polarization characteristics, the durability, and the like, an acetate-based resin such as triacetylcellulose is preferable, and in particular a triacetylcellulose film whose surface has been subjected to saponization process with an alkali is preferable.

The thickness of the polarizer protective layer is arbitrary; however, typically the thickness is 500 μm or below, preferably 1 to 300 μm, more preferably 5 to 200 μm, for the purpose of thickness reduction of the polarizing plate. Here, in the event that the polarizer protective layer made of a transparent film is disposed on both surfaces of the polarizing film, transparent films made of different polymers or the like may be used on the front and rear surfaces.

The polarizer protective layer may be subjected to a hard-coating process, an antireflection process, processes performed for the purposes of preventing or diffusing sticking, or antiglaring. The hard-coating process is carried out for the purpose of preventing scars to be formed on the polarizing plate surface, and the hard-coating can be formed by adding a cured skin film being excellent in hardness or slipping property made by an ultraviolet-curing resin such as a silicone-based one onto the surface of the transparent protective film.

On the other hand, the antireflection process is carried out for the purpose of preventing reflection of external light on the polarizing plate surface, and can be achieved by forming an antireflection film according to the prior art. Also, the sticking preventing process is performed for the purpose of preventing close adhesion to adjacent layers, and the antiglaring process is carried out for the purpose of preventing hindrance of the visibility of the light transmitted through the polarizing plate caused by reflection of external light on the surface of the polarizing plate, and can be formed, for example, by imparting a fine undulation structure on the surface of the transparent protective film by a suitable method such as the surface roughening treatment by the sandblast method or the emboss processing method, or the method of blending transparent fine particles.

The above-described transparent fine particles may be, for example, silica, alumina, titanium, zirconia, tin oxide, indium oxide, cadmium oxide, antimony oxide, or the like having an average particle size of 0.5 to 20 μm. Inorganic fine particles having an electric conductivity may be used, and organic fine particles made of crosslinked or non-crosslinked polymer particulate substances may be used. The amount of using the transparent fine particles is typically 2 to 70 parts by mass, preferably 5 to 50 parts by mass, relative to 100 parts by mass of the transparent resin.

Further, the antiglaring layer blended with the transparent fine particles can be provided as the transparent protective layer itself or as a layer applied onto the surface of the transparent protective layer. The antiglaring layer may also serve as a diffusing layer for enlarging the viewing angle (viewing angle compensating function) by diffusing the light transmitted through the polarizing plate. Here, the antireflection layer, the sticking preventing layer, the diffusing layer, the antiglaring layer, and the like described above may be provided separately from the transparent protective layer as optical layers made of sheets on which those layers are disposed.

In practical use, the sheet-shaped product according to the present invention can be used as an optical film by laminating various optical layers. The optical layers are not particularly limited; however, an example is a method of performing a hard-coating process, an antireflection process, surface treatments performed for the purposes of preventing sticking, diffusing, or antiglaring, or laminating a oriented liquid crystal layer for the purpose of viewing angle compensation or the like. Also, examples of the optical layer are those obtained by bonding one layer or two or more layers of an optical film used for forming a liquid crystal display device such as a reflection plate, a semitransparent plate, a retardation plate (including a wavelength plate (plate) such as ½ or ¼), or a viewing angle compensating film. In particular, when the sheet-shaped product is a polarizing plate, it can be preferably applied as a reflection-type polarizing plate or a semi-transmitting type polarizing plate made by lamination of a reflecting plate or a semitransmitting plate, an elliptic or circular polarizing plate made by lamination of a retardation plate, a wide viewing angle plate made by lamination of a viewing angle compensating layer or a viewing angle compensating film, or a polarizing plate made by lamination of a brightness-improving film.

The reflection type polarizing plate is one in which a reflection layer is provided in a polarizing plate, and is used for forming a liquid crystal display device of a type that displays by reflecting incident light coming from the visible side (display side), and has advantages such as facilitated thickness reduction of the liquid crystal display device because incorporation of a light source such as back light can be omitted. The reflection-type polarizing plate can be formed, for example, by a suitable method such as additionally disposing a reflection layer made of metal or the like on one surface of a polarizing plate via a transparent protective layer in accordance with the needs.

A specific example of a reflection-type polarizing plate is a plate in which a reflection layer is formed by additionally disposing a foil or a vapor-deposited film made of a reflective metal such as aluminum on one surface of a transparent protective film subjected to a matting process in accordance with the needs. Also, another example is a plate having a surface fine undulating structure obtained by allowing fine particles to be contained in the above-described transparent protective film and further having a reflection layer of fine undulating structure thereon. The above-described reflection layer of fine undulating structure has advantages of preventing directivity or glittering appearance by diffusing the incident light by random reflection and restraining unevenness of brightness and darkness. Also, the transparent protective film containing fine particles has advantages of further restraining the unevenness of brightness and darkness because the incident light and the reflected light thereof are diffused when passing through the film. The reflection layer having a fine undulating structure on which the surface fine undulating structure of the transparent protective film is reflected can be formed, for example, by directly adding metal to the surface of the transparent protective layer by a suitable method such as a vapor deposition method such as the vacuum vapor deposition method, ion plating method, or the sputtering method, or the plating method.

The reflection plate can also be used as a reflection sheet in which a reflection layer is disposed on a suitable film that accords to the transparent film in place of directly imparting to the transparent film (polarizer protective film) of the above-described polarizing plate. Herein, since the reflection layer is typically made of metal, the usage mode in a state in which the reflection surface thereof is covered with a transparent film or a polarizing plate is preferable in view of preventing decrease in the reflectivity caused by oxidation, and further the long-term durability of the initial reflectivity, and the avoidance of separately disposing a protective layer.

Herein, the semitransmitting polarizing plate can be obtained by making a reflection layer of semitransmittance type such as a half mirror that reflects and transmits light at the reflection layer in the above construction. The semitransmittance type polarizing plate is typically disposed on the back surface of a liquid crystal cell, and can form a liquid crystal display device or the like of a type such that, in the event that a liquid crystal display device or the like is used in a comparatively bright atmosphere, images are displayed by reflecting the incident light coming from the visible side (display side) and, in a comparatively dark atmosphere, images are displayed by using an incorporated light source such as a back light unit that is incorporated on the back side of the semitransmitting type polarizing plate. Namely, the semitransmitting type polarizing plate is useful for forming a liquid crystal display device of a type that can save the energy of using the light source such as a back light unit in a bright atmosphere and can be used by using an incorporated light source even in a comparatively dark atmosphere.

The elliptic polarizing plate or the circular polarizing plate made by further laminating a retardation plate on a polarizing plate will be described. A retardation plate or the like is used in the case of converting linearly polarized light into elliptically polarized light or circularly polarized light, converting elliptically polarized light or circularly polarized light into linearly polarized light, or changing the polarization direction of linearly polarized light. In particular, as a retardation plate that converts linearly polarized light into circularly polarized light or converts circularly polarized light into linearly polarized light, a so-called ¼ wavelength plate (also referred to as λ/4 plate) is used. A ½ wavelength plate (also referred to as λ/2 plate) is used typically for changing the polarization direction of linearly polarized light.

The elliptic polarizing plate is effectively used for compensating (preventing) the coloring (blue or yellow) generated by birefringence of the liquid crystal layer of a super twist nematic (STN) type liquid crystal display device, so as to perform white and black display without the above-described coloring. Further, those that control the three-dimensional refractive index can compensate (prevent) the coloring generated when the screen of the liquid crystal display device is viewed in an oblique direction, so that it is preferable. The circular polarizing plate is effectively used, for example, for regulating the color tone of the images of the reflection-type liquid crystal display device in which the images are displayed in color, and also has a function of preventing reflection.

Another example thereof is a retardation. As the retardation plate, a birefringent film obtained by monoaxial or biaxial stretching of a polymer material, an oriented film of liquid crystal polymer, one in which the oriented layer of liquid crystal polymer is supported by a film, and the like. The stretching process can be carried out, for example, by roll stretching method, long gap stretching method, tenter stretching method, tubular stretching method, or the like. The magnification of stretching is typically about 1.1 to 3 times in the case of monoaxial stretching. The thickness of the retardation plate is not particularly limited; however, the thickness is typically 10 to 200 μm, preferably 20 to 100 μm.

Examples of the above-described polymer material are polyvinyl alcohol, polyvinyl butyral, polymethyl vinyl ether, polyhydroxyethyl acrylate, hydroxyethylcellulose, hydroxypropylcellulose, methylcellulose, polycarbonate, polyallylate, polysulfone, polyethylene terephthalate, polyethylene naphthalate, polyethersulfone, polyphenylene sulfide, polyphenylene oxide, polyallylsulfone, polyvinyl alcohol, polyamide, polyimide, polyolefin, polyvinyl chloride, cellulose-based polymer, and various two-element or three-element copolymers, graft copolymers, and blended products of these. These polymer materials are made into an oriented product (stretched film) by stretching or the like.

Examples of the above-described liquid crystal polymer are various polymers of main chain type or side chain type in which a conjugate linear atomic group (mesogen) that imparts liquid crystal orientation property is introduced the main chain or the side chain of the polymer. Specific examples of the liquid crystalline polymer of main chain type are, for instance, a polyester-based liquid crystalline polymer having, for example, a nematic orientation property, a discotic polymer, or a cholesteric polymer having a structure such that the mesogen groups are bonded with a spacer part that imparts a bending property. Specific example of a liquid crystal polymer of side chain type are, for instance, those having polysiloxane, polyacrylate, polymethacrylate, or polymalonate as a main chain skeleton and having a mesogen part made of a para-substituted cyclic compound unit having a nematic orientation imparting property via a spacer part made of a conjugate atomic group as the side chain. These liquid crystalline polymers are carried out, for example, by developing a solution of liquid crystalline polymer on an orientation-processed surface of those obtained by a rubbing treatment, tilted vapor deposition of silicon oxide, or the like of the surface of a thin film such as polyimide or polyvinyl alcohol formed on a glass plate, followed by a thermal treatment.

The retardation plate may be a plate having a suitable retardation in accordance with an intended object of use such as various wavelength plates and those intended for compensation of coloring or viewing angle caused by birefringence of the liquid crystal layer, or may be those in which the optical characteristics such as the retardation are controlled by laminating two or more kinds of retardation plates.

The viewing angle compensating film is a film for enlarging the viewing angle so that the images can be looked at comparatively vividly even in a case in which the screen of the liquid crystal apparatus is looked at not vertically to the screen but in a little oblique direction. Examples of such a viewing angle compensating retardation plate are those in which an oriented layer of liquid crystal polymer or the like is supported on an oriented film or a transparent base material such as a retardation film or a liquid crystal polymer. In a typical retardation plate, a polymer film having birefringence that has been monoaxially stretched in the plane direction thereof is used. However, in a retardation plate used as a viewing angle compensating film, a polymer film having birefringence that has been biaxially stretched in the plane direction or a two-direction stretched film such as a polymer film having birefringence with the refractive index controlled in the thickness direction that has been monoaxially stretched in the plane direction and also stretched in the thickness direction or a tilted orientation film is used. Examples of tilted orientation film are those obtained by bonding a heat-shrinking film on a polymer film and performing a stretching process and/or a shrinking process on the polymer film under the action of the shrinking force thereof caused by the heating, or those obtained by oblique orientation of a liquid crystal polymer. The source material polymer of the retardation plate may be one similar to the polymer described in the previous retardation plate, and a suitable source material polymer intended for a purpose such as preventing the coloring or the like caused by change in the viewing angle based on the retardation due to the liquid crystal cell or enlarging the viewing angle can be used.

Also, in view of achieving a wide viewing angle having a good visibility, an optical compensating retardation plate in which an optically anisotropic layer made of an oriented layer of a liquid crystal polymer, particularly a tilted orientation layer of a discotic liquid crystal polymer, is supported by a triacetylcellulose film is preferably used.

A polarizing plate obtained by bonding a polarizing plate with a brightness-improving film is typically used by being disposed on the back side of a liquid crystal cell. The brightness-improving film is a film exhibiting a property of reflecting the linearly polarized light of a predetermined polarization axis or a circularly polarized light of a predetermined direction and transmitting the other light when natural light is incident by a back light unit of a liquid crystal display device or the like or reflection from the back side. The polarizing plate obtained by lamination of a brightness-improving film with a polarizing plate allows light from a light source such as a back light unit to be incident so as to obtain a transmitted light of a predetermined polarization state, and the light other than those in the predetermined polarization state is reflected without being transmitted. The light reflected on this brightness-improving film surface is allowed to be incident again into the brightness-improving film by reversing the light via a reflection layer or the like disposed further in the rear, and a part or a whole thereof is transmitted as the light in the predetermined polarization state, so as to increase the amount of the light that is transmitted through the brightness-improving film, and the polarized light that can be hardly absorbed by the polarizer is supplied so as to increase the amount of light usable for liquid crystal display image display or the like, whereby the brightness can be improved. Namely, in the event that the light is made to be incident through the polarizer from the back side of the liquid crystal cell by a back light unit or the like without using the brightness-improving film, most of the light having a polarization direction that is not coincident with the polarization axis of the polarizer will be absorbed by the polarizer and will not be transmitted through the polarizer. Namely, though differing in accordance with the characteristics of the polarizer to be used, about 50% of the light is absorbed by the polarizer, so that the amount of light that can be used for liquid crystal image display or the like will decrease for that amount, and the images will be dark. The brightness-improving film repeats the process of temporarily reflecting the light having a polarization direction that is liable to be absorbed by the polarizer without allowing the light to be incident into the polarizer and further reflecting the light via a reflection layer or the like disposed further in the rear so as to allow the light to be incident again into the brightness-improving film. Therefore, the brightness-improving film transmits only the light in which the polarization direction of the light that is reflected and reversed between these two has become a polarization direction capable of passing the polarizer, so as to supply the light to the polarizer, whereby the light of the back light unit or the like can be efficiently used for displaying images of the liquid crystal display device, and the screen can be made brighter.

A diffusing plate can be disposed between the brightness-improving film and the above-described reflection layer. The light in the polarization state reflected by the brightness-improving film will proceed towards the above-described reflection layer, and the disposed diffusing layer diffuses the passing light uniformly and eliminates the polarization state so as to achieve a non-polarized state. Namely, the diffusing plate turns the polarized light into the original natural light state. The light in this non-polarized state, namely, the natural light state, repeats the process of proceeding towards the reflection layer or the like, being reflected via the reflection layer or the like, passing through the diffusing plate, and being incident again into the brightness-improving film. By disposing a diffusing plate that turns the polarized light into the original natural light state between the brightness-improving plate and the above-described reflection layer in this manner, the unevenness of the brightness of the display screen can be reduced while maintaining the brightness of the display screen, whereby a uniform and bright screen can be provided. By disposing such a diffusing plate, it seems that the number of repetition of the reflection of the initial light increases to a good amount and, in combination with the diffusing function of the diffusing plate, a uniform and bright screen can be provided.

As the above-described brightness-improving plate, suitable brightness-improving plates such as those exhibiting a property of transmitting the linearly polarized light of a predetermined polarization axis and reflecting the other light such as a multiple-layer thin film of dielectrics or a thin film having a different refractive index anisotropy, or those exhibiting a property of reflecting the circularly polarized light of either one of rightward rotation or leftward rotation and transmitting the other light such as one in which an oriented film of cholesteric liquid crystal polymer or an oriented liquid crystal layer thereof is supported on a film base material.

Therefore, in a type of the above-described brightness-improving film that transmits the linearly polarized light of a predetermined polarization axis, by allowing the transmitted light to be incident as it is into the polarizing plate while arranging the polarization axis, the light can be transmitted efficiently while restraining the absorption loss caused by the polarizing plate. On the other hand, in the brightness-improving film of a type that transmits the circularly polarized light such as a cholesteric liquid crystal layer, the light can be allowed to be incident as it is into the polarizer; however, in view of restraining the absorption loss, the circularly polarized light is preferably allowed to be incident into the polarizer after being converted into linearly polarized light via a retardation plate. Herein, by using a ¼ wavelength plate as the retardation plate, the circularly polarized light can be converted into linearly polarized light.

The retardation plate functioning as the ¼ wavelength plate in a wide wavelength range such as a visible light band can be obtained, for example, by a method of superposing a retardation plate functioning as a ¼ wavelength plate to faint color light of a wavelength of 550 nm and a retardation plate exhibiting a different retardation property, for example, a retardation plate functioning as the ½ wavelength plate. Therefore, the retardation plate to be placed between the polarizing plate and the brightness-improving plate may be made of retardation layers of one layer or two or more layers.

Further, regarding the cholesteric liquid crystal layer, by making a combination of those differing in the reflection wavelength to provide a placement structure in which two or three or more layers are superposed, one can obtain those that reflect circularly polarized light in a wide wavelength range such as a visible light band and, on the basis thereof, a transmitted circularly polarized light in a wide wavelength range can be obtained.

Also, the sheet-shaped product (for example, a polarizing plate) of the present invention may be made of a lamination of a polarizing plate and optical layers of two layers or three or more layers, such as the above-described polarization separating type polarizing plate. Therefore, it may be a reflection-type elliptic polarizing plate or a semitransmitting type elliptic polarizing plate in which the above-described reflection-type polarizing plate or semitransmitting-type polarizing plate is combined with a retardation plate.

An optical film in which the above-described optical layer is laminated on a polarizing plate can be formed by a method of sequentially separately laminating in a production process of the liquid crystal display device; however, an optical film made by lamination in advance is excellent in the stability of the product quality and the assembling work, thereby providing an advantage of improving the production process of the liquid crystal display device. For the lamination, a suitable bonding means such as an adhesive layer can be used. In bonding the above-described polarizing plate with the other optical layers, the optical axes thereof can be in a suitable placement angle in accordance with the retardation property or the like.

In the polarizing plate according to the present invention or the above-described laminated optical members, an adhesive layer for bonding to another member such as a liquid crystal cell is disposed. The adhesive layer is not particularly limited; however, it can be formed with a suitable adhesive agent that accords to the prior art such as an acryl-based adhesive agent. It is preferably an adhesive layer having a low moisture-absorbing property and being excellent in the heat resistance in view of preventing the foaming phenomenon caused by absorption of moisture or a peeling-off phenomenon, preventing decrease in the optical characteristics or warpage of the liquid crystal cell caused by thermal expansion difference or the like, and further a property of forming an image displaying apparatus having a high product quality and being excellent in durability. Also, the adhesive layer may be made to exhibit a light-diffusing property by containing fine particles. The adhesive layer may be disposed on a needed surface in accordance with the needs. For example, referring to a polarizing plate made of a polarizer and a polarizer protective layer, the adhesive layer may be disposed on one surface or on both surfaces of the polarizer protective layer in accordance with the needs.

On the exposed surface of the above-described adhesive layer, a separator (also referred to as a release film) is provisionally attached for covering for the purpose of preventing the contamination thereof until it is subjected to practical use. This can prevent contact with the adhesive layer in an ordinary and usual state of handling. As the separator, one can use a suitable one that accords to the prior art, for example, those in which a suitable thin leaf-like body such as a plastic film, a rubber sheet, paper, cloth, non-woven cloth, a net, a foamed sheet, a metal foil is coated with a suitable release agent such as a silicone-based one, a long-chain-alkyl-based one, a fluorine-based one, or molybdenum sulfide in accordance with the needs, excluding the above-described thickness condition.

On the polarizing plate that is the opposite surface to the surface on which this separator is disposed, a protective film is formed via a weak adhesive agent. The object thereof is mainly for prevention of scars and prevention of contamination. As the protective film, suitably used are protective films according to the prior art, for example, those in which a suitable thin leaf-like body such as a plastic film, a rubber sheet, paper, cloth, non-woven cloth, a net, a foamed sheet, a metal foil is coated with a suitable release agent such as a silicone-based one, a long-chain-alkyl-based one, a fluorine-based one, or molybdenum sulfide in accordance with the needs.

Here, in the present invention, each layer of the polarizer, the polarizer protective film, or the optical film that form the above-described polarizing plate, as well as the adhesive layer, may be made to have, for example, an ultraviolet-absorbing property by a method such as treating with an ultraviolet absorber such as a salicylate-based compound, a benzophenol-based compound, benzotriazol-based compound, cyanoacrylate-based compound, or a nickel-complex-salt-based compound.

The sheet-shaped product of the present invention can be preferably used for forming an image displaying apparatus (corresponding to an optical display device) such as a liquid crystal display device, an organic EL display device, or a PDP.

The polarizing plate or the optical film of the present invention can also be preferably used for forming various apparatus such as a liquid crystal display device. The liquid crystal display device can be formed according to the prior art. Namely, a liquid crystal display device is typically formed by suitably assembling construction components such as a liquid crystal cell (corresponding to an optical display unit), a polarizing plate or an optical film, and an illumination system or the like in accordance with the needs, followed by incorporating a driving circuit. In the present invention, there is no particular limitation except that the polarizing plate or the optical film of the present invention is used, so that it can be carried out according to the prior art. Regarding the liquid crystal cell also, those of any type such as a TN type, an STN type, or a π type can be used, for example.

A suitable liquid crystal display device can be formed such as a liquid crystal display device in which the polarizing plate or the optical film is disposed on one side or on both sides of the liquid crystal cell, or a liquid crystal display device in which a back light unit or a reflection plate is used in an illumination system. In that case, the polarizing plate or the optical film of the present invention can be disposed on one side or on both sides of the liquid crystal cell. In the event that the polarizing plate or the optical film is disposed on both sides, they may be the same or different. Further, in forming the liquid crystal display device, for example, suitable components such as a diffusing plate, an antiglaring layer, a reflection preventive film, a protective plate, a prism array, a lens array sheet, a light-diffusing plate, or a back light unit can be disposed as one layer or as two or more layers at a suitable position.

The sheet-shaped product (for example, a polarizing plate) according to the present invention can be preferably used for forming various apparatus such as a liquid crystal display device. The liquid crystal display device can be formed to have a suitable structure according to the prior art of transmittance type, a reflection type, or a combined type of transmittance and reflection in which the sheet-shaped product (for example, a polarizing plate) according to the present invention is disposed on one side or on both sides of the liquid crystal cell. Therefore, the liquid crystal cell that constitutes the liquid crystal display device is arbitrary and, for example, it may be one that uses a liquid crystal cell of a suitable type such as a simple matrix driving type represented by a thin film transistor type, for example.

Also, in the event that the polarizing plate or the optical member is disposed on both sides of the liquid crystal cell, they may be the same or different. Further, in forming the liquid crystal display device, for example, suitable components such as a prism array sheet, a lens array sheet, a light-diffusing plate, or a back light unit can be disposed as one layer or as two or more layers at a suitable position.

<Construction of Test Data Processing Apparatus>

Embodiment 1

Figure 1:
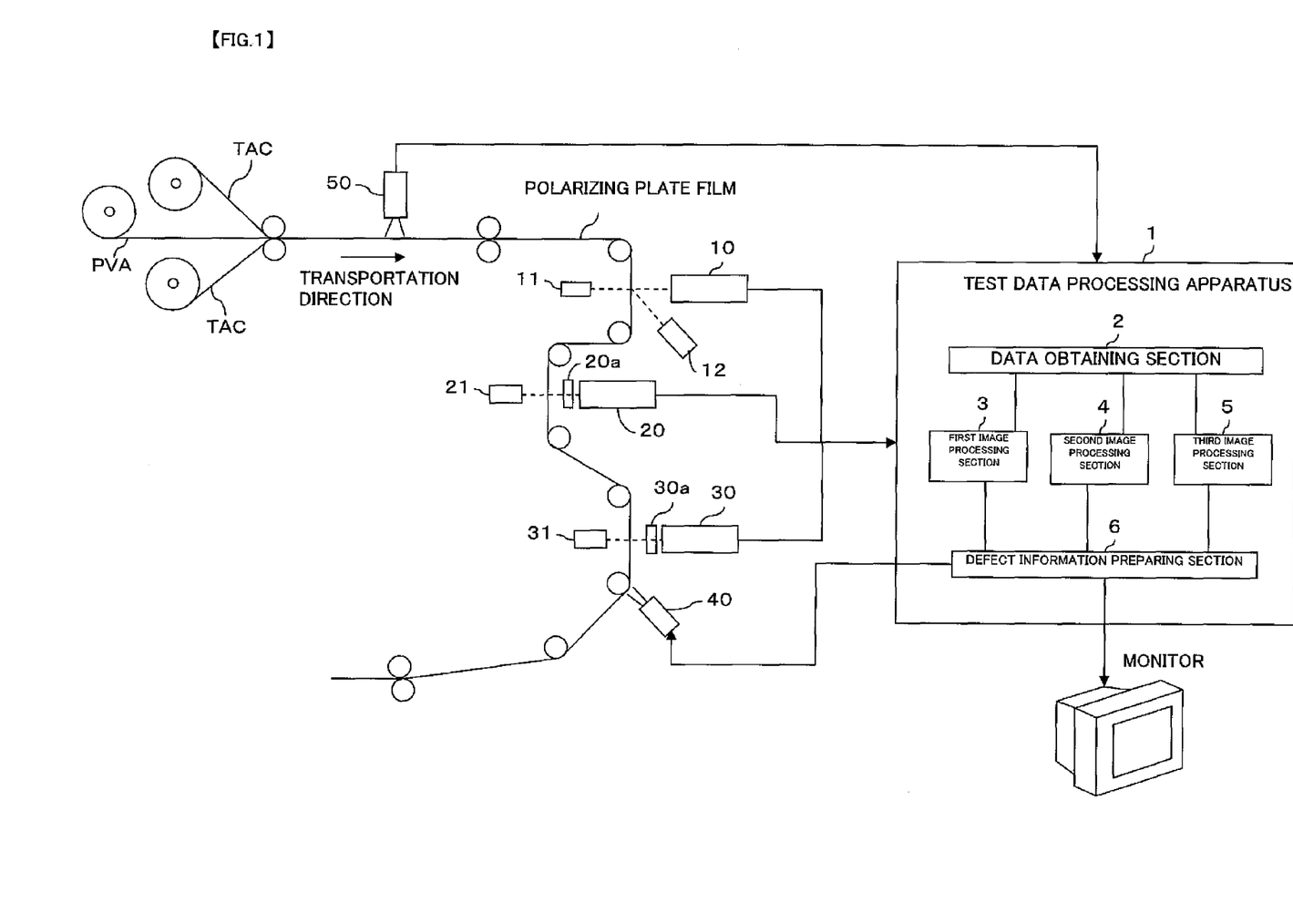
FIG. 1 is a block diagram showing the functions of a test data processing apparatus.

Hereinafter, a construction of a test data processing apparatus of the present invention will be described with reference to the attached drawings. FIG. 1 is a functional block diagram of the test data processing apparatus. In the functional description of FIG. 1, means and the like exhibiting the functions and effects of the present invention will be mainly described, so that the description of conventionally known means will be omitted or simplified. In the following, for the sake of description, the steps of producing a polarizing plate (TAC/PVA/TAC) will be described; however, the present invention is not limited to this alone. Also, detection by a testing apparatus of defects relating to surface-adhering foreign substances that adhere to the surface during the production steps but are removed in or before the final winding step may be referred to as erroneous detection (or excessive detection).

In FIG. 1, on the upstream side of the steps, a PVA film is drawn out from a PVA source roll and, after the PVA film is subjected to various processes not illustrated, a TAC film is bonded onto both surface sides thereof. The TAC film is drawn out from a source roll thereof, is subjected to various processes not illustrated, and is subjected to application of an adhesive agent before the bonding step. These various processes may be carried out on a continuous line; however, they may be carried out on separate lines.

The test data processing apparatus 1 includes a data obtaining section 2, a first image processing section 3, a second image processing section 4, a third image processing section 5, and a defect information preparing section 6. Also, it is necessary that the test data processing apparatus 1 includes at least the data obtaining section 2 and the defect information preparing section 6. In this case, it is constructed in such a manner that the defect information is received from each testing means (constructed with a light source, an image capturing section, and an image processing section), and the defect information preparing section 6 prepares the integrated defect information.

The data obtaining section 2 can be constructed with known communication means, regardless of whether it is wireless or wired. The data obtaining section 2 receives the position information (coordinates) that has been read by a bar code (for example, a QR-code or the like) reading apparatus 50. Also, the data obtaining section 2 receives individual captured image data from a first image capturing section 10, a second image capturing section 20, and a third image capturing section 30. The image position (position coordinates) of the captured image data can be calculated from the obtained position information and the transportation speed of the polarizing plate by a later-mentioned image processing section. The data obtaining section 2 may have a function of receiving various data and dividing the data into different destinations of transmittance, and may be constructed to have a plurality of receiving lines whereby the image capturing section and the image processing section corresponding thereto are directly connected with each other.

The first, second, third image capturing sections 10, 20, 30 can be constructed, for example, with one or two or more CCD cameras. The first image capturing section 10 can alternately capture transmitted light image by a LED light source 11 and a reflected light image by a halogen light source 12.

The first image processing section 3 receives a captured image signal of the first image capturing section 10 via the data obtaining section 2. The first image processing section 3 analyzes the captured image data (transmitted light image, reflected light image), and determines the defects. The size, the shape, and the kind of the defects can be determined, and this can be realized with a known algorithm. By performing image processing on a transmitted light image, a foreign substance located in the inside can be detected and determined. Also, by performing image processing on a reflected light image, a surface-adhering foreign substance can be detected and determined.

The second image capturing section 20 can capture a transmitted light image by a halogen light source 21. In the process, a polarization filter 20a for testing is disposed between the halogen light source 21 and the second image capturing section 20. The polarization filter 20a for testing is disposed to form a predetermined angle (for example, a range larger than 0 degrees and smaller than or equal to 10 degrees) with the polarization axis of the polarizing plate which is an object of testing (x degree cross). The second image processing section 4 receives the captured image signal of the second image capturing section 20 via the data obtaining section 2, and performs image processing on this captured image. This allows that the knicks located inside the polarizing plate can be detected and determined. As the algorithm for the image processing, a known one can be applied.

The third image capturing section 30 can capture a transmitted light image by a halogen light source 31. At this time, a polarization filter 30a for testing is disposed between the halogen light source 31 and the third image capturing section 30. The polarization filter 30a for testing is disposed in crossed nicol with the polarization axis of the polarizing plate which is an object of testing (0 degree cross). The third image processing section 5 receives the captured image signal of the third image capturing section 30 via the data obtaining section 2, and performs image processing on this captured image. This allows that the defects of the polarizing plate can be detected and determined as bright points. As the algorithm for the image processing, a known one can be applied. Herein, also the surface-adhering foreign substances detected by the first image capturing section 10 are detected as bright points. Namely, in different two testing steps, an identical foreign substance is detected in duplication. Then, the surface-adhering foreign substance is removed naturally (or forcibly) in the final production step, so that, if the polarizing plate is cut on the basis of the information of such erroneously detected defects, the yield will be poor, hence not preferable.

Figure 3:
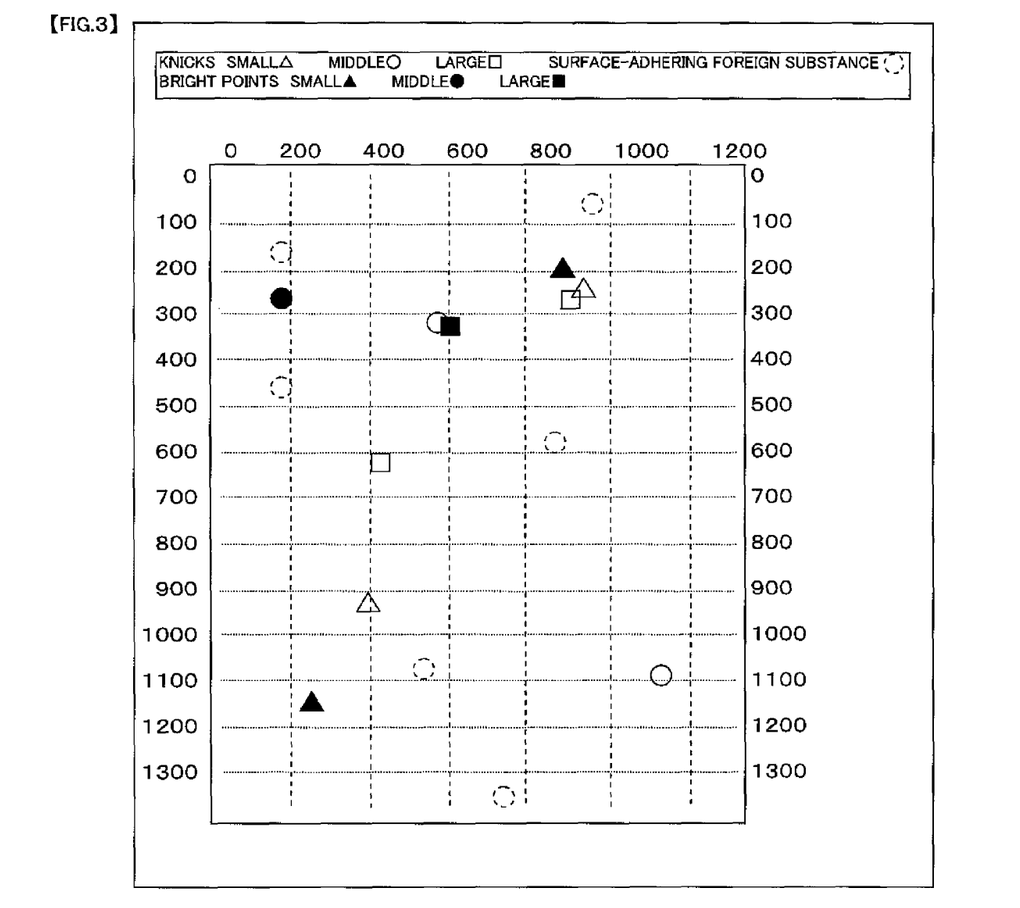
FIG. 3 is a view showing a display example of the defect information.

The defect information preparing section 6 of the present invention obtains information of the defects that have been detected (determined) in the first, second, third image processing sections 3, 4, 5, and prepares defect information so as not to raise the above-described problem. Namely, the defect information is prepared by not treating the erroneously detected defects as defects. The prepared defect information can be displayed on a monitor. FIG. 3 shows one example of the defect information displayed on the monitor. Together with the width of the source and the coordinates in the longitudinal direction, the knicks and the bright points are displayed by being classified into different sizes. Though the surface-adhering foreign substances are not determined as defects, they can be shown as circular marks drawn in a broken line. This owes to the function of the display controlling means (not illustrated). Also, the defect information can be converted into a QR-code, which is then transmitted to the code forming apparatus 40 and can be supplied to form a QR-code at a predetermined pitch (for example 1000 mm).

The defect information includes, for example, the kind of the defects, the position coordinates thereof, the production identification information, the test object identification information, and the like. The position coordinates may be relative coordinates from a predetermined base point, or may be absolute coordinates using the tip end part of the source as the base point.

Specifically, regarding the information of defects obtained from a reflected light image that has been captured by the first image capturing section 10 and the information of defects obtained from a bright point image that has been captured (0 degree cross) by the third image capturing section 30, the defects having identical position coordinates are not regarded as a defect. More preferably, the defects located at identical coordinates and having identical or approximately identical sizes of the defects are not regarded as defects. Most preferably, the defects located at identical coordinates and having identical or approximately identical sizes and shapes of the defects are not regarded as defects. FIG. 2 shows a procedure of preparing the defect information and the prepared defect information. First, (1) the results of the information of defects by reflected light image and the information of defects by 0 degree cross are compared, and the defects having identical coordinates are not regarded as defects (in FIG. 2, coordinates (x1, y1)). Also, as another embodiment, the defects located at identical coordinates and having identical or approximately identical sizes of the defects are not regarded as defects (in FIG. 2, coordinates (x3, y3)). Also, as still another embodiment, the defects located at identical coordinates and having identical or approximately identical sizes and shapes of the defects are not regarded as defects (in FIG. 2, coordinates (x4, y4)). Herein, for the sake of description, the modes of not treating as defects have been assumed to be three kinds; however, for example, the determination can be made by any one kind of the determination condition. Next, (2) the data that have been determined in (1) and not treated as defects are removed from the information of the defects by reflected light image and 0 degree cross. Further, the defect information is prepared by including the information of defects by the transmitted light image and the information of the defects by x degree cross.

The defect information preparing section 6 integrates the obtained information of the defects and the position information (position coordinates) of the defects, and prepares defect information as a polarizing plate source. For example, the defect information can be prepared so that knicks and internal foreign substances may be contained at identical coordinates. Also, even if plural kinds of defects are present at identical coordinates, the defect information can be prepared by regarding them as only either one kind (for example, internal foreign substance). The defects detected at an identical position can be integrated so that all of them may be included.

According to the above-described embodiment, the defect information can be prepared by not regarding the surface-adhering foreign substances that will not eventually adhere to the product source as a defect, and the product source can be cut according to an accurate defect information in cutting the product source into a sheet-shaped product provided in separate sheets, thereby greatly improving the yield.

Also, since the number of defects caused by surface-adhering foreign substances is large, data processing abilities (such as memory size and processing speed) have been needed; however, according to the present invention, since the number of defects can be reduced to a great extent, the data processing efficiency will be improved.

Embodiment 2

The test data processing apparatus of the present invention can be realized by collaboration function of software and hardware (CPU, memory, and the like), and can also be realized by an exclusive-use circuit, firmware, or the like, or a combination of these.

In the case of realizing the test data processing apparatus with software, the program thereof will be as follows. This program may be recorded in a recording medium, may be suppliable as a recording medium, or may be supplied via a communication line (supplying by downloading). In the event that the program is supplied via a communication line, only a part of the functions may be supplied, and the other part of the functions may remain in a server apparatus, so that the construction is included within the technical scope of the present invention as long as the functions of the present invention are exhibited as a total function.

The software program of the present invention is a program for allowing a computer to execute a processing step in which, on the basis of surface defect test data relating to a surface defect and bright point test data relating to a bright point obtained when a laminate body containing an optical film is regarded as an object of testing, in a case that a position of the surface defect and a position of the bright point are identical, the surface defect and the bright point located at the identical position are not regarded as a defect.

Another Embodiment

The present invention has been described on a sheet-shaped product including a polarizing plate. However, the present invention is not limited to this alone, and can be applied to a laminate body of a polarizing plate and a retardation plate, a retardation plate, and a polarizer (PVA) alone. The present invention can be applied to test data processing of a testing system in which the detection of bright points and the detection of defects by reflected light image are combined.

What is claimed is:

1. A test data processing apparatus for processing test data obtained by testing defects of a sheet-shaped product having at least an optical film which is a member of an optical displaying apparatus, comprising:
    an image capturing section for capturing image data of a long sheet-shaped product while the long sheet-shaped product is fed;
    an image data processing section for analyzing the image data captured by the image capturing section and determining the defects;
    a defect information preparing section for preparing a defect information based on information of the detects determined by the image data processing section;
    wherein the defect information preparing section prepares the defect information in such a way that on the basis of surface defect test data relating to a surface defect and bright point test data relating to a bright point obtained when the optical film or a laminate body containing the optical film is regarded as an object of testing,
    wherein the surface defect test data is obtained based on a reflected light image of a surface of the object of testing,
    wherein the bright point test data is obtained based on a transmitted light image which pass through the object of testing and a polarization filter for testing which is disposed in crossed nicol with the polarization axis of the object of testing, and
    wherein, in a case that a position of the surface defect and a position of the bright point are identical, the surface defect and the bright point located at the identical position are not regarded as a defect for processing by the defect information preparing section;
    wherein the image capturing section comprising:

first image capturing section for capturing transmitted light image without a polarization filter for a testing and reflected light image of the long sheet-shaped product; and third image capturing section for capturing transmitted light image with a polarization filter for a testing, the polarization filter is disposed between a light source and the second image capturing section and the polarization axis of a polarization filter is disposed to form in crossed nicol with the polarization axis of the long sheet-shaped product.

2. The test data processing apparatus according to claim 1, wherein, when the defect and the bright point located at an identical position have an identical or approximately identical size and/or shape, the surface defect and the bright point located at the identical position are not regarded as a defect for processing by the test data processing apparatus.

3. The test data processing apparatus according to claim 2, wherein the defect information preparing section prepares defect information as at least one type of defects in a case that a position of the bright point is identical to a position of a knick located inside of the object of testing obtained on the basis of the transmitted light image of the object of testing by interposing, therebetween, the polarization filter for testing which is disposed with respect to the polarization axis of the object of testing at an angle that is larger than 020 and not more than 10°.

4. The test data processing apparatus according to claim 1, wherein the optical film is a polarizer.

5. The test data processing apparatus according to claim 1, wherein the defect information preparing section prepares defect information as at least one type of defects in a case that a position of the bright point is identical to a position of a knick located inside of the object of testing obtained on the basis of the transmitted light image of the object of testing by interposing, therebetween, the polarization filter for testing which is disposed with respect to the polarization axis of the object of testing at an angle that is larger than 0° and not more than 10°.

6. The test data processing apparatus according to claim 1, further comprising; a display section for displaying the defect information prepared by the defect information preparing section.

7. The test data processing apparatus according to claim 5, wherein the image capturing section comprising;
second image capturing section for capturing transmitted light image with a polarization filter for a testing, the polarization filter is disposed between a light source and the second image capturing section and the polarization axis of a polarization filter is disposed to form a predetermined angle with the polarization axis of the long sheet-shaped product.

8. The test data processing apparatus according to claim 1, wherein the defect information preparing section prepares the defect information in such a way that a position of the surface defect and a position of the bright point are identical, the surface defect and the bright point located at the identical position are not regarded as a defect for processing;

wherein the position of the surface defect based on reflected light image is captured by first image capturing section, and wherein the position of the bright point based on transmitted light image is captured by third image capturing section.

9. A test data processing method for processing test data obtained by testing defects of a sheet-shaped product having at least an optical film which is a member of an optical displaying apparatus, comprising:

an image capturing step that comprises capturing image data of a long sheet-shaped product while the long sheet-shaped product is fed;

an image data processing step that comprises analyzing the image data captured by the image capturing section and determining the defects;

a defect information preparing step that comprises preparing a defect information based on information of the detects determined by the image data processing section;

wherein the defect information preparing step prepares the defect information in such a way that on the basis of surface defect test data relating to a surface defect and bright point test data relating to a bright point obtained when the optical film or a laminate body containing the optical film is regarded as an object of testing, wherein the surface defect test data is obtained based on a reflected light image of a surface of the object of testing, wherein the bright point test data is obtained based on a transmitted light image which pass through the object of testing and a polarization filter for testing which is disposed in crossed nicol with the polarization axis of the object of testing, and wherein, in a case that a position of the surface defect and a position of the bright point are identical, the surface defect and the bright point located at the identical position are not regarded as a defect for processing;

wherein the image capturing step comprising:

capturing, by first image capturing section, transmitted light image without a polarization filter for a testing and reflected light image of the long sheet-shaped product; and capturing, by third image capturing section, transmitted light image with a polarization filter for a testing, the polarization filter is disposed between a light source and the second image capturing section and the polarization axis of a polarization filter is disposed to form in crossed nicol with the polarization axis of the long sheet-shaped product.

10. The test data processing method according to claim 9, wherein, when the defect and the bright point located at an identical position have an identical or approximately identical size and/or shape, the surface defect and the bright point located at the identical position are not regarded as a defect for processing.

11. The test data processing method according to claim 9, wherein the optical film is a polarizer.

* * * * *